United States Patent
Mascal et al.

(10) Patent No.: US 10,399,953 B2
(45) Date of Patent: Sep. 3, 2019

(54) PREPARATION OF FURAN FATTY ACIDS FROM 5-(CHLOROMETHYL)FURFURAL

(71) Applicant: THE REGENTS OF THE UNIVERSITY OF CALIFORNIA, Oakland, CA (US)

(72) Inventors: Mark Mascal, Oakland, CA (US); Fei Chang, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/751,809

(22) PCT Filed: Sep. 14, 2016

(86) PCT No.: PCT/US2016/051765
§ 371 (c)(1),
(2) Date: Feb. 9, 2018

(87) PCT Pub. No.: WO2107/048864
PCT Pub. Date: Mar. 23, 2017

(65) Prior Publication Data
US 2018/0230118 A1   Aug. 16, 2018

Related U.S. Application Data

(60) Provisional application No. 62/218,361, filed on Sep. 14, 2015.

(51) Int. Cl.
*A23L 33/12* (2016.01)
*C07D 307/54* (2006.01)

(52) U.S. Cl.
CPC ............ *C07D 307/54* (2013.01); *A23L 33/12* (2016.08)

(58) Field of Classification Search
CPC .................................................. C07D 307/54
USPC ........................................................ 549/499
See application file for complete search history.

(56) References Cited

U.S. PATENT DOCUMENTS

| 4,009,187 | A | * | 2/1977 | Eliasson | ............... C07D 307/16 549/488 |
|---|---|---|---|---|---|
| 4,559,392 | A | | 12/1985 | Grundmann | |
| 5,492,915 | A | | 2/1996 | Dereu et al. | |
| 5,747,537 | A | | 5/1998 | Gordon et al. | |
| 9,868,712 | B2 | * | 1/2018 | Mascal | ............... C07D 307/36 |
| 2012/0302774 | A1 | | 11/2012 | Kim et al. | |

(Continued)

FOREIGN PATENT DOCUMENTS

| EP | 110548 A1 | | 6/2001 |
|---|---|---|---|
| GB | 1195324 | * | 6/1970 |
| JP | 62153218 | * | 7/1987 |

(Continued)

OTHER PUBLICATIONS

Glass; Lipids, 1975, 10, 695-702. (Year: 1975).*

(Continued)

*Primary Examiner* — Daniel R Carcanague
(74) *Attorney, Agent, or Firm* — Mintz, Levin, Cohn, Ferris, Glovsky and Popeo, P.C.

(57) ABSTRACT

The present invention provides methods of making furfural fatty acids from (chloromethyl)furfural. The present invention also provides furfural fatty acids and nutritional supplements that include furfural fatty acids.

12 Claims, 2 Drawing Sheets

(56) References Cited

U.S. PATENT DOCUMENTS

2016/0207895 A1* 7/2016 Mascal ............... C07D 307/36

FOREIGN PATENT DOCUMENTS

WO     WO2002067929     *   9/2002
WO     WO-2014179156 A1 * 11/2014 ........... C07D 307/48

OTHER PUBLICATIONS

Jie; Chemistry and Physics of Lipids 1978, 21, 275-287. (Year: 1978).*
Soler-Yanes; European Journal of Organic Chemistry 2014, 6625-6629. (Year: 2014).*
Jie; Lipids, 1991, 26, 837-841. (Year: 1991).*
Jie; Lipids 2003, 38, 1293-1297. (Year: 2003).*
Evans; ARKIVOC 2008, 10, 95-102. (Year: 2008).*
Rahn; Lipids 1981, 16, 360-364. (Year: 1981).*
Masamune; Bulletin of the Chemical Society of Japan 1975, 48, 491-496. (Year: 1975).*
Chang; Sustainable Chemistry and Pharmacy 2015, 1, 14-18. First available online Oct. 23, 2015. http://dx.doi.org/10.1016/j.scp.2015.09.002 (Year: 2015).*
Bailey; J. Org. Chem., 1956, 21, 297-303. (Year: 1956).*
International Searching Authority at the United States Patent and Trademark Office, International Search Report and Written Opinion for International Patent Application No. PCT/US2016/051765, dated Nov. 4, 2016, 9 pages.
Hammann, Analysis of Intact Cholestryl Esters of Furan Fatty Acids in Cod Liver, Lipids, Apr. 28, 2015, pp. 611-620, abstract, vol. 50.
Chang, et al., Synthesis of the Insecticide Prothrin and Its Analogues from Biomass-Derived 5-(Chloromethyl)furfural, Journal of Agricultural and Food Chemistry, 2014, pp. 476-480, 477, abstract, vol. 62.
Hoffmann, The Quest for Chiral Grignard Reagents, Chemical Society Reviews, 2003, pp. 225-230, 225, 227, vol. 32.
Pubchem. CID 18795072, Dec. 4, 2007, pp. 1-9 [online] Retrieved on Oct. 21, 2016, from https://pubchem.ncbi,nim.nih.gov/compound/18795072.
Bach et al., "Sequential Pd(0)-Catalyzed Reactions for the Construction of Multiple Substituted Furans. A Short Synthesis of the F5 Furan Fatty Acid", 1998, vol. 39, No. 13, pp. 1729-1732.
Batna et al., "The occurrence of furan fatty acids in *Isochrysis* sp. and Phaeodactylum tricornutum", Biochimica et Biophysica Acta—Lipids and Lipid Metabolism, 1993, vol. 1166, No. 2-3, pp. 171-176.
Batna et al., "Effects of soybean lipoxygenase-1 on phosphatidylcholines containing furan fatty acids", Lipids, 1994, vol. 29, No. 6, pp. 397-403.
Boselli et al., "Determination of Furan Fatty Acids in Extra Virgin Olive Oil", 2000, vol. 48, No. 7, pp. 2868-2873.
Buchta et al., "10.13-Dihydroxy-hexadecansäure-methyleste r und Hexadecantriol-(1.10.13)", Justus Liebigs Annalen der Chemie, 1967, vol. 704, No. 1, pp. 115-119.
Buchta et al., "Über die Darstellung langkettinger Carbonsäuren unter Verwendung von Vinyl-[[omega]-alkoxycarbonyl-alkyl]-ketonen, VIII. Dioxo-, Trioxo- und Tetraoxo-margarinsäuren mit 1.4-ständigen Oxo-Gruppen und Margarinsäure", Justus Liebigs Annalen der Chemie, 1966, pp. 93-100.
Buchta et al., "Über die Darstellung langkettinger Carbonsauren unter Verwendung von Vinyl-[omega-alkoxycarbonyl-alkyl]-ketonen, V. Dioxo-, Trioxo- stearinsauren mit 1.4-ständigen Oxo-Gruppen und Stearinsäure", Justus Liebigs annalen derChemie, 1965, vol. 686, No. 1, pp. 77-87.
Dembitsky et al., "Furan fatty acids of some brackish invertebrates from the Caspian Sea", Comparative Biochemistry and Physiology Part B: Biochemistry and Molecular Biology, 1996, vol. 114, No. 3, pp. 317-320.
Dietel et al., "Inkubation von 2,5-disubstituierten F-Säuren mit Rinderleberhomogenisat", Liebigs Annalen der Chemie, 1988, vol. 1988, No. 5, pp. 397-403.
Doering et al., "Toxicity of Myristic Acid Analogs Toward African Trypanosomes", Proceedings of the National Academy of Sciences of the United States of America, 1994, vol. 91, No. 21, pp. 9735-9739.
Ellamar et al., "One-Step Production of a Biologically Active Novel Furan Fatty Acid from 7,10-Dihydroxy-8€-octadecenoic Acid", Journal of Agricultural and Food Chemistry, 2011, vol. 59, No. 15, pp. 8175-8179.
Extended European Search Report for EP Appl. No. 16847246.2, dated Feb. 2, 2019.
Gunstone et al., "The component acids of lipids from marine and freshwater species with special reference to furan-containing acids", Journal of the Science of Food and Agriculture, 1978, vol. 29, No. 6, pp. 539-550.
Guth et al., "Furanfettsäuren in Butter und Butterschmalz", Zeitschrift fuer Lebensmitteluntersuchung und-Forschung, 1992, vol. 194, No. 4, pp. 360-362.
Jie et al., "Synthesis of dimethyl-substituted C18 furanoid fatty ester", Journal of the American Oil Chemists' Society, 1992, vol. 69, No. 5, pp. 485-487.
Okajima et al., "Studies on lipids of crayfish, *Procambarus clarkia*. I. Furanoid fatty acids", Chemical and Pharmaceutical bulletin, 1984, vol. 32, No. 8, pp. 3281-3286.
Pacetti et al., "Characterisation of furan fatty acids in Adriatic fish", 2010, vol. 22, No. 1, pp. 209-215.
Scheinkonig et al., "Methylation of the β-positions of the furan ring in F-acids", Biochimica et Biophysca Acta—Lipids and Lip Metabolism, 1995, vol. 1254, No. 1, pp. 73-76.
Teixeira et al., "Furan fatty acids efficiently rescue brain cells from cell death induced by oxidative stress", Food & Function, 2013, vol. 4, No. 8, pp. 1209-1215.
Wahl et al., "Identification of fatty acid methyl esters as minor components of fish oil by multidimensional GC-MSD: New furan fatty acids", Journal of High Resolution Chromatography, 1994, vol. 17, No. 5, pp. 308-311.
Wakimoto et al., "Furan fatty acid as an anti-inflammatory component from the green-lipped mussel *Pema canaliculus*", Proceedings of the National Academy of Sciences of the United States of America, 2011, vol. 108, No. 42, pp. 17533-17537.
Wendlinger et al., "High Concentrations of Furan Fatty Acids in Organic Butter Samples from the German Market", Journal of Agricultural and Food Chemistry, 2014, vol. 62, No. 34, pp. 8740-8744.

* cited by examiner

PREPARATION OF FURAN FATTY ACIDS FROM 5-(CHLOROMETHYL)FURFURAL

CROSS-REFERENCES TO RELATED APPLICATIONS

This application is the U.S. National Stage Entry under § 371 of International Application No PCT/US2016/051765, filed Sep. 14, 2016, which claims the benefit of U.S. Provisional Application No. 62/218,361, filed Sep. 14, 2015, each of which is incorporated in its entirety herein for all purposes.

STATEMENT AS TO RIGHTS TO INVENTIONS MADE UNDER FEDERALLY SPONSORED RESEARCH AND DEVELOPMENT

Not Applicable

BACKGROUND OF THE INVENTION

The modern concept of the biorefinery is characterized by the production of fuels, commodity chemicals, and value-added products from non-petroleum based carbon sources (Clark and Deswarte (2015) In *Introduction to Chemicals from Biomass, Second Edition*. 1-29). There is a strong movement in the physical and biological sciences in support of the biorefinery concept, established around the proposition that the unabated use of all current fossil fuel reserves will have serious, potentially irreversible environmental consequences (McGlade and Ekins (2015) *Nature* 517: 187). The synthesis of value-added products (e.g., agrochemicals and healthcare products) from biomass feedstocks is a key strategy within this movement to leverage business models organized principally around low-margin, high-volume commodities such as biofuels and polymers.

Examples of such value-added products include healthcare products for individuals suffering from atherosclerosis. Atherosclerosis is a chronic inflammatory condition which is the primary cause of cardiovascular diseases that account for about half of the mortalities in developed countries (Lusis (2000) *Nature* 407: 233). Diets rich in fish and marine organisms are recognized to have an anti-atherosclerotic effect (Calder (2004) *Clin. Sci.* 107:1; Biscione et al. (2007) *Curr. Vasc. Pharmacol.* 5: 163; and von Schaky (2007) *Curr. Opin. Clin. Nutr. Metab. Care* 10:129). While the polyunsaturated omega-3 fatty acids eicosapentaenoic acid (EPA) and docosahexaenoic acid (DHA) are credited to be the active components of fish oil, furan fatty acids (FFAs) are now also believed to play a significant role (Vetter and Wendlinger (2013) *Lipid Technol.* 25: 7; and Spiteller (2005) *Lipids* 40:775). For example, it has been demonstrated that FFAs exhibit a greater anti-inflammatory effect than EPA in arthritis models (Wakimoto et al. (2011) *Proc. Natl. Acad. Sci.* 108: 17533). It has even been theorized that FFAs, rather than omega-3 acids, are responsible for the cardioprotective effects of fish consumption (Glass et al. (1975) *Lipids* 10: 695). Multiple in-vitro antioxidant studies of FFAs have demonstrated that the compounds suppress lipid peroxidation by scavenging radicals and singlet oxygen species (Ishii et al. (1989) *Chem. Pharm. Bull.* 37: 1396), suggesting applications in the management of hyperlipidemia (Tsuji and Wakimoto (2009) Jpn. Kokai Tokkyo Koho JP2009062315), autoimmune disorders (Tsuji and Wakimoto (2009) Jpn. Kokai Tokkyo Koho JP2009062314), and dermatitis (Tsuji and Wakimoto (2009) Jpn. Kokai Tokyo Koho JP2009062316). Recent studies also show that FFAs can effectively rescue brain cells from cell death induced by oxidative stress (Teixeira et al. (2013) *Food Funct.* 4: 1209), while other work has even pointed to potential anti-tumor activity (Isoda et al. (1993) *J. Japan Oil Chem. Soc.* 42: 923).

FFAs from marine sources were first isolated and structurally characterized in 1974 (Glass et al (1994) *Lipids* 9: 1004; and Glass et al. (1975)). All marine FFAs are typified by a long fatty acid chain at the 2-position of the furan ring and a $C_3$ or $C_5$ alkyl chain at the 5-position. One or both of the remaining positions of the ring ($R^1$, $R^2$) may be substituted with a methyl group. Due to their low natural abundance and sensitivity to isolation procedures, a number of synthetic approaches to these compounds have been reported. Since FFAs are biogenetically derived by the oxidation of lipids (Batna and Spiteller (1991) *Liebigs Ann. Chem.* 861; and Shirasaka et al. (1997) *Biochim. Biophys. Acta* 1346: 253), the most evident synthetic route would be via the corresponding unsaturated $C_{16}$-$C_{20}$ acids. Thus, Ellamar and co-workers submitted oleic acid to microbial oxidation with *Pseudomonas aeruginosa* PR3 to give 7,10-dihydroxy-8-octadecenoic acid, which could be thermally cyclized to an unnatural FFA (FIG. 1, 5, n=6, m=4, $R^1$=$R^2$=H), the antioxidant activity of which was low (Ellamar et al. (2011) *J. Agric. Food Chem.* 59: 8175). A simpler approach was reported by Yurawecz et al., who aerated a sample of linoleic acid at 50° C. over the course of several hours to give a mixture of FFAs, albeit with very low conversion (Yurawecz et al. (1995) *Lipids* 30: 595). Lie Ken Jie and Ahmad adapted a method for producing unmethylated FFAs via epoxidation of doubly unsaturated fatty acids (Gunstone and Schuler (1975) *Chem. Phys. Lipids* 15: 174) to generate a mixture of dimethyl FFAs in five steps via oxidation of methyl linoleate, again however in low overall yield (Lie Ken Jie and Ahmad (1981) *J. Chem. Soc. Chem. Comm.* 1110).

More efficient, total synthetic approaches to FFAs have also been described by various groups. The first reported synthesis of a natural furan fatty acid pre-dates their isolation from fish, instead referring to the observation of FFA (FIG. 1, 5 n=4, m=6, $R^1$=$R^2$=H) in the seeds of a sandalwood shrub (Morris et al. (1966) *Tetrahedron Lett.* 4249). The route encompasses five steps starting from furoic acid with a total yield of <10% (Elix and Sargent (1968) *J. Chem. Soc.* 595). Other efforts towards unmethylated FFAs include hydration of octadecadiynoate esters (Lie Ken Jie and Lam (1977) *Chem. Phys. Lipids* 19: 275), and multistep approaches via furan, furfural, and furfuryl alcohol (Lie Ken Jie and Lam (1978) *Chem. Phys. Lipids* 21: 275; and Buchta and Huhn (1965) *Liebigs Ann. Chem.* 686: 77).

The first total synthesis of the methylated FFAs was reported by Rahn and co-workers, and was 5-6 steps from the advanced starting materials 3,4-bis-(acetoxymethyl)furan and methyl 3-methyl-2-furoate (Rahn and Sand (1979) *J. Org. Chem.* 44: 3420). Marson and Harper employed an unconventional approach starting from cycloundecanone, which could be converted to 5 of FIG. 1 (n=3, m=9, $R^1$=H, $R^2$=Me) in 6 steps and 13% overall yield (Marson and Harper (1998) *Tetrahedron Lett.* 39: 333; and Marson and Harper (1998) *J. Org. Chem.* 63: 9223). A contribution by Bach and Kruger showcases a Pd(0)-catalyzed coupling between a 10-undecynoate ester and 4,5-dibromofurfural, followed by Wittig olefination, methylation with MeZnCl, and finally hydrogenation to 5 of FIG. 1 (n=3, m=9, $R^1$=H, $R^2$=Me) in 28% overall yield (Bach and Kruger (1998) *Tetrahedron Lett.* 39: 1729; and Back and Kruger (1999) *Eur. J. Org. Chem.* 2045). Finally, Knight et al. described syntheses of both monomethylated (n=3, m=9, $R^1$=H, $R^2$=Me) and dimethylated 5 of FIG. 1 (n=3, m=9, $R^1$=$R^2$=Me) starting from the mono-TBS derivative of 1,12-dodecanediol, which was converted into an alkyne diol precursor for Ag(I)-catalyzed cyclization to the furan products. The overall route involved 8-9 steps in 40 and 32% yields, respectively (Evans et al. (2008) *ARKIVOC* 95). A later optimization of this route starting from 10-undecenal provided the same FFAs in improved yields (63 and 48%, respectively) by employing gold(III) catalysis, among other minor variations (Knight and Smith (2012) *Heterocycles* 84: 361). All of the above syntheses suffer either from low yields or the use of expensive starting materials or reagents.

Previous work successfully accomplished the syntheses of the natural herbicide δ-aminolevulinic acid 2 of FIG. 1 (Mascal and Dutta (2011) *Green Chem.* 13: 40), the anti-ulcer drug ranitidine (Zantac) 3 of FIG. 1 (Mascal and Dutta (2011) *Green Chem.* 13: 3101), and the furan-based pyrethroid insecticide prothrin 4 of FIG. 1 (Chang et al. (2014) *J. Agric. Food Chem.* 62: 476) from the renewable platform molecule 5-(chloromethyl)furfural (CMF) 1 of FIG. 1, which can be derived in a single step from sugars, cellulose, or raw biomass in isolated yields as high as 80% (Mascal and Nikitin (2008) *Angew. Chem. Int. Ed.* 47: 7924; and Mascal and Nikitin (2009) *ChemSusChem* 2: 859). The present invention surprisingly meets the need for a high-yielding approach to naturally occurring and biologically active FFAs, as well as other needs, by demonstrating the additional synthesis of FFAs from this CMF platform.

BRIEF SUMMARY OF THE INVENTION

In one embodiment, the present invention provides methods of preparing a compound of Formula I having the structure:

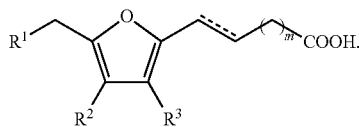
(I)

The method includes forming a first reaction mixture including an alcohol and a compound of Formula II:

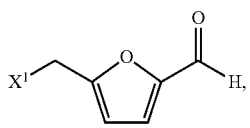
(II)

under conditions sufficient to form a compound of Formula III:

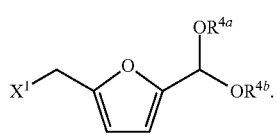
(III)

$X^1$ is halogen, and $R^{4a}$ and $R^{4b}$ are $C_{1-18}$ alkyl. The method further includes forming a second reaction mixture including an alkylating agent with a formula $R^1ML_n$, and a compound of Formula I, under conditions sufficient to form a compound of Formula IV:

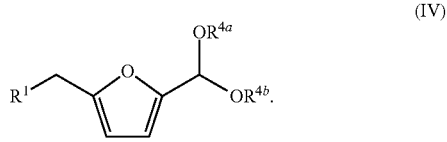
(IV)

M is a metal, L is a ligand, and n is an integer from 1 to 3. The method further includes forming a third reaction mixture including an aqueous acid and a compound of Formula IV, under conditions sufficient to form a compound of Formula V:

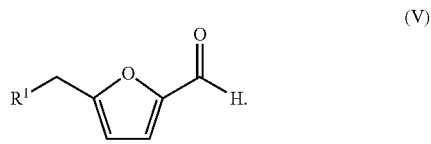
(V)

The method further includes forming a fourth reaction mixture including a phosphonium salt of Formula VI:

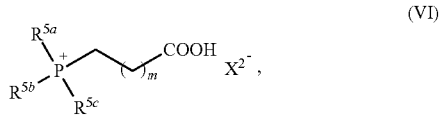
(VI)

and a compound of Formula V, under conditions sufficient to form the compound of Formula I. $R^{5a}$, $R^{5b}$, and $R^{5c}$ can each independently be H, $C_{1-18}$ alkyl, $C_{2-18}$ alkenyl, or $C_{6-12}$ aryl. $R^2$ and $R^3$ can each independently be H or $C_{1-6}$ alkyl. $X^2$ is halogen, $R^1$ is $C_{1-18}$ alkyl, and m is an integer from 1 to 18.

In a second embodiment, the present invention provides compounds having the structure of Formula I wherein $R^1$ is $C_{1-18}$ alkyl, m is an integer from 1-18, and $R^2$ and $R^3$ can each independently be H or $C_{1-6}$ alkyl.

In a third embodiment, the present invention provides nutritional supplements including a compound having the structure of Formula I wherein $R^1$ is $C_{1-18}$ alkyl, m is an integer from 1-18, and $R^2$ and $R^3$ can each independently be H or $C_{1-6}$ alkyl.

DETAILED DESCRIPTION OF THE INVENTION

I. General

Figure 1:
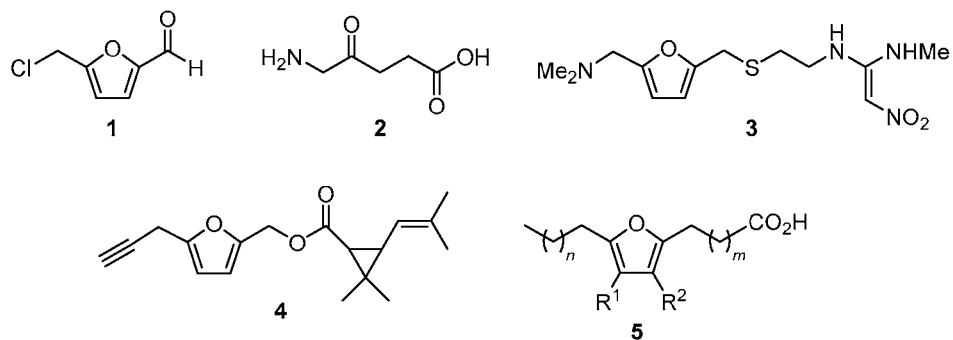
FIG. 1 illustrates chemical structures of molecules synthesized using the renewable platform molecule 5-(chloromethyl)furfural as a starting material.

The present invention provides methods of preparing furan fatty acids (FFAs) from 5-chloromethyl(furfural) (CMF). The present invention also provides FFA compounds and nutritional supplements including one or more FFA compounds.

II. Definitions

The abbreviations used herein have their conventional meaning within the chemical and biological arts.

"Fatty acid" refers to a carboxylic acid having an aliphatic tail, typically from 4 to 30 carbon atoms long. Fatty acids can be saturated, mono-unsaturated or poly-unsaturated. Fatty acids useful in the present invention also include branched fatty acids such as iso-fatty acids. Examples of fatty acids useful in the present invention, include, but are not limited to, butyric acid (C4), caproic acid (C6), caprylic acid (C8), capric acid (C10), lauric acid (C12), myristic acid (C14), palmitic acid (C16), palmitoleic acid (C16), stearic acid (C18), isostearic acid (C18), oleic acid (C18), vaccenic acid (C18), linoleic acid (C18), alpha-linoleic acid (C18), gamma-linolenic acid (C18), arachidic acid (C20), gadoleic acid (C20), arachidonic acid (C20), eicosapentaenoic acid (C20), behenic acid (C22), erucic acid (C22), docosahexaenoic acid (C22), lignoceric acid (C24) and hexacosanoic acid (C26). One of skill in the art will appreciate that other fatty acids are useful in the present invention.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Halogen" refers to fluorine, chlorine, bromine and iodine.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Metal" refers to elements of the periodic table that are metallic and that can be neutral, or negatively or positively charged as a result of having more or fewer electrons in the valence shell than is present for the neutral metallic element. Metals useful in the present invention include the alkali metals, alkali earth metals, transition metals and post-transition metals. Alkali metals include Li, Na, K, Rb and Cs. Alkaline earth metals include Be, Mg, Ca, Sr and Ba. Transition metals include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Post-transition metals include Al, Ga, In, TI, Ge, Sn, Pb, Sb, Bi, and Po. Rare earth metals include Sc, Y, La, Ce, Pr, Nd, Sm, Eu, Gd, Tb, Dy, Ho, Er, Tm, Yb and Lu. One of skill in the art will appreciate that the metals described above can each adopt several different oxidation states, all of which are useful in the present invention. In some instances, the most stable oxidation state is formed, but other oxidation states are useful in the present invention.

"Acid" refers to a compound that is capable of donating a proton (H) under the Bronsted-Lowry definition, or is an electron pair acceptor under the Lewis definition. Acids useful in the present invention are Bronsted-Lowry acids that include, but are not limited to, alkanoic acids or carboxylic acids (formic acid, acetic acid, citric acid, lactic acid, oxalic acid, etc.), sulfonic acids and mineral acids, as defined herein. Mineral acids are inorganic acids such as hydrogen halides (hydrofluoric acid, hydrochloric acid, hydrobromice acid, etc.), halogen oxoacids (hypochlorous acid, perchloric acid, etc.), as well as sulfuric acid, nitric acid, phosphoric acid, chromic acid and boric acid. Sulfonic acids include methanesulfonic acid, benzenesulfonic acid, p-toluenesulfonic acid, triflouromethanesulfonic acid, camphorsulfonic acid, among others.

"Alcohol" refers to an alkyl group, as defined within, having a hydroxy group attached to a carbon of the chain. For example, alcohol includes, but is not limited to, methanol, ethanol, propanol, isopropanol, butanol, isobutanol, tert-butanol, pentanol and hexanol, among others. Alcohols useful in the present invention are fully saturated. One of skill in the art will appreciate that other alcohols are useful in the present invention.

"Alkylating agent" refers to a material that selectively alkylates a starting molecule by adding a desired aliphatic carbon chain to the molecule. An alkylating agent can be nucleophilic alkylating agent, an electrophilic alkylating agent, or a carbene. Examples of alkylating agents include organometallic compounds, and alkyl halides used with a Lewis acid catalyst.

"Ligand" refers to an ion or functional group of a molecule that binds to a central metal atom to form a coordination complex. A ligand can be, for example, an amine, a phosphine, CO, $N_2$, an alkene, or halogen.

"Forming a reaction mixture" refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

"Nutritional supplement", "dietary supplement", and "nutraceutical" refer to foods or food ingredients that provide to a subject health or medical benefits beyond those associated with the basic caloric value of the food. A nutritional supplement can be administered to or taken by a subject to provide, supply, or increase one or more nutrients. The one or more nutrients can be, for example, a vitamin, mineral, trace essential element, amino acid, peptide, nucleic acid, oligonucleotide, lipid, cholesterol, steroid, fatty acid, antioxidant, or a carbohydrate.

"Food" refers to an edible substance to be ingested orally. A food can be, for example, a beverage or a non-beverage. A food can be, for example, a sweet, a confectionary, a nutrient, or a pharmaceutical.

"Subject" refers to animals such as mammals, including, but not limited to, primates (e.g., humans), cows, sheep, goats, horses, dogs, cats, rabbits, rats, mice and the like. In certain embodiments, the subject is a human.

"Edible" as used herein refers to a substance that can be eaten by animals or humans. The term encompasses substances that are deemed non-toxic and can be orally ingested and tolerated.

"First", "second", and "third" when used herein are simply to more clearly distinguish the two or more elements or properties and are not intended to indicate order.

III. Methods of Preparing Furan Fatty Acid Compounds

Described here a synthetic route to FFA natural products with the biorefinery platform molecule CMF at their core. The approach incorporates sufficient versatility to provide FFAs of different chain lengths on either the 2- or 5-positions of the furan ring, and to produce either unalkylated or dialkylated versions of FFAs. The application of bromomethylation in the synthesis also provides functional handles for the production of novel FFA analogues with substituents other than methyl groups in the 3- and 4-positions. No expensive reagents are involved in the synthesis and all reactions proceed in high yields (average 93%), giving the approach distinct advantages over published routes, which may promote the future commercialization of these remarkable antioxidants as nontoxic foodstuff preservatives or nutraceutical alternatives to diets heavy in fish (Mozaffarian and Rimm (2006) *J. Am. Med. Assoc.* 296: 1885; Jackson et al. (2001) *Science* 293: 629).

The present invention provides several methods of preparing FFA compounds having the structure of Formula I:

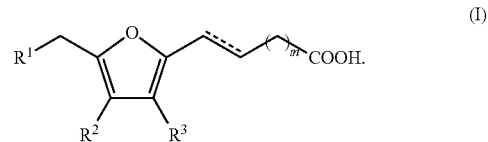

$R^1$ can be $C_{1-18}$ alkyl, $R^2$ and $R^3$ can each independently be H or $C_{1-6}$ alkyl, and m can be an integer from 1 to 18. The methods include forming a first reaction mixture including an alcohol and a compound having the structure of Formula II:

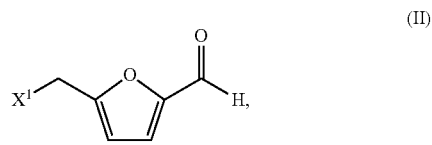

under conditions sufficient to form a compound of Formula III:

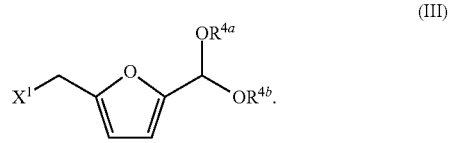

$X^1$ is halogen, and $R^{4a}$ and $R^{4b}$ can be $C_{1-18}$ alkyl. The methods further include forming a second reaction mixture including an alkylating agent with a formula $R^1ML_n$, and a compound having the structure of Formula III, under conditions sufficient to form a compound having the structure of Formula IV:

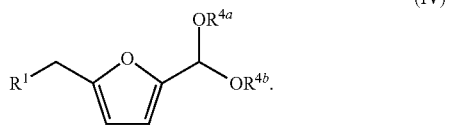

(IV)

M is a metal, L is a ligand, and n is an integer from 1 to 3. The methods further include forming a third reaction mixture including an aqueous acid and a compound of Formula IV, under conditions sufficient to form a compound having the structure of Formula V:

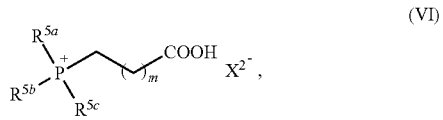

(V)

The methods further include forming a fourth reaction mixture including a phosphonium salt having the structure of Formula VI:

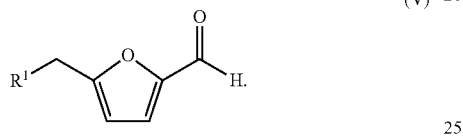

(VI)

and a compound having the structure of Formula V, under conditions sufficient to form the compound having the structure of Formula I. $X^2$ is halogen, and $R^{5a}$, $R^{5b}$, and $R^{5c}$ can each independently be H, $C_{1-18}$ alkyl, $C_{2-18}$ alkenyl, or $C_{6-12}$ aryl.

The alcohol of the first reaction mixture can be, for example methanol, ethanol, propanol, isopropanol, butanol, isobutanol, tert-butanol, pentanol or hexanol. The alcohol can be propanol, butanol, or pentanol. In some embodiments, the alcohol is butanol.

$R^1$ of Formula I can be $C_{1-18}$ alkyl. In some embodiments, $R^1$ is methyl, ethyl, or propyl. In some embodiments, $R^1$ is ethyl. $R^2$ and $R^3$ of Formula I can each independently be H or $C_{1-6}$ alkyl. In some embodiments, $R^2$ is H. In some embodiments, $R^2$ is methyl. In some embodiments, $R^3$ is H. In some embodiments, $R^3$ is methyl. In some embodiments, both $R^2$ and $R^3$ are H. In some embodiments, both $R^2$ and $R^3$ are methyl. Integer m of Formula I can be 1-18. In some embodiments, integer m is 6, 8, or 10. In some embodiments, integer m is 8.

$X^1$ of Formula II can be fluorine, chlorine, bromine, or iodine. In some embodiments, $X^1$ is chlorine. $R^{4a}$ and $R^{4b}$ of Formula III can be $C_{1-18}$ alkyl. In some embodiments, $R^{4a}$ and $R^{4b}$ are ethyl, propyl, butyl, or pentyl. In some embodiments $R^{4a}$ and $R^{4b}$ are butyl.

The metal of the alkylating agent can be, for example, magnesium, lithium, copper, or sodium. In some embodiments, the metal of the alkylating agent is magnesium. The ligand of the alkylating agent can be halogen. In some embodiments, the ligand of the alkylating agent is chloride.

Integer n of the alkylating agent formula can be 1, 2, or 3. In some embodiments, integer n is 1. In some embodiments, the alkylating agent has the formula $R^1MgX^3$, wherein $X^3$ is halogen. In some embodiments, the alkylating agent is ethylmagnesium chloride.

The aqueous acid of the third reaction mixture can be, for example, perchloric acid, hydrochloric acid, sulfuric acid, phosphoric acid, or acetic acid. In some embodiments, the aqueous acid of the third reaction mixture is hydrochloric acid. $R^{5a}$, $R^{5b}$, and $R^{5c}$ of Formula VI can be H. $R^{5a}$, $R^{5b}$, and $R^{5c}$ of Formula VI can be $C_{1-18}$ alkyl. $R^{5a}$, $R^{5b}$, and $R^{5c}$ of Formula VI can be $C_{2-18}$ alkenyl. $R^{5a}$, $R^{5b}$, and $R^{5c}$ of Formula VI can be $C_{6-12}$ aryl. In some embodiments, $R^{5a}$, $R^{5b}$, and $R^{5c}$ are each phenyl.

$X^2$ of Formula VI can be fluorine, chlorine, bromine, or iodine. In some embodiments, $X^2$ is iodine.

In some embodiments, the method of preparing FFA compounds further includes forming a fifth reaction mixture including hydrogen, a first hydrogenation catalyst, and the compound of Formula I having the structure:

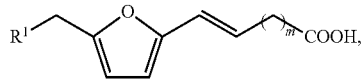

under conditions sufficient to form the compound of Formula I having the structure:

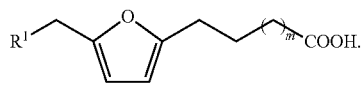

The first hydrogenation catalyst can be a homogeneous or heterogeneous catalyst. The catalyst can comprise platinum, palladium, rhodium, ruthenium, or nickel. In some embodiments, the first hydrogenation catalyst is palladium on carbon.

In some embodiments, the method of preparing FFA compounds further includes forming a sixth reaction mixture including formaldehyde or paraformaldehyde, hydrogen bromide, and the compound of Formula I having the structure:

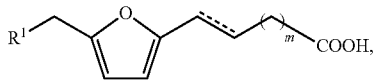

under conditions sufficient to form a compound of Formula VII:

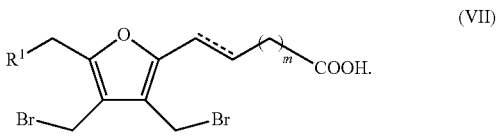

(VII)

The method further includes forming a seventh reaction mixture including hydrogen, a second hydrogenation catalyst, and a compound having the structure of Formula VII under conditions sufficient to form the compound of Formula I having the structure:

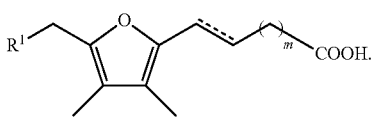

In some embodiments, the sixth reaction mixture includes formaldehyde. In some embodiments, the sixth reaction mixture includes paraformaldehyde.

The second hydrogenation catalyst can be a homogeneous or heterogeneous catalyst. The catalyst can comprise platinum, palladium, rhodium, ruthenium, or nickel. In some embodiments, the second hydrogenation catalyst is palladium on carbon.

In some embodiments, the compound of Formula I has the structure

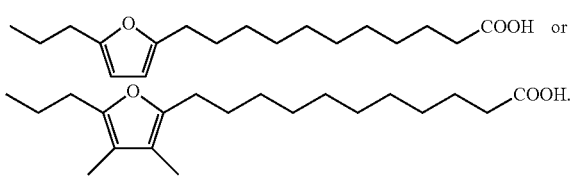

In some embodiments, the compound of Formula I has the structure

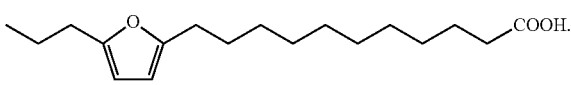 [SMILES: CCCc1ccc(CCCCCCCCCCC(=O)O)o1]

In some embodiments, the compound of Formula I has the structure

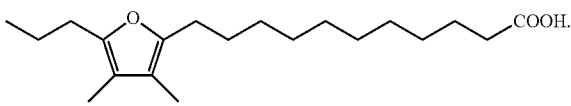 [SMILES: CCCc1oc(CCCCCCCCCCC(=O)O)c(C)c1C]

IV. Furan Fatty Acid Compounds

In some embodiments, the present invention provides several FFA compounds. In some embodiments, the present invention provides compounds of Formula I having the structure:

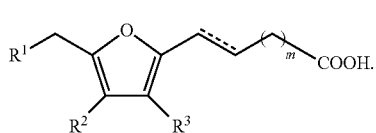

$R^1$ of Formula I can be $C_{1-18}$ alkyl. In some embodiments, $R^1$ is methyl, ethyl, or propyl. In some embodiments, $R^1$ is ethyl. $R^2$ and $R^3$ of Formula I can each independently be H or $C_{1-6}$ alkyl. In some embodiments, $R^2$ is H. In some embodiments, $R^2$ is methyl. In some embodiments, $R^3$ is H. In some embodiments, $R^3$ is methyl. In some embodiments, both $R^2$ and $R^3$ are H. In some embodiments, both $R^2$ and $R^3$ are methyl. Integer m of Formula I can be 1-18. In some embodiments, integer m is 6, 8, or 10. In some embodiments, integer m is 8.

In some embodiments, the compound of Formula I has the structure

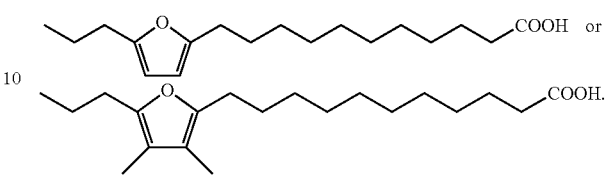

In some embodiments, the compound of Formula I has the structure

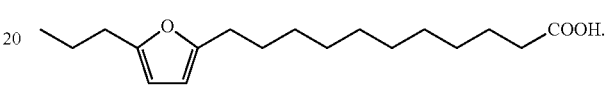

In some embodiments, the compound of Formula I has the structure

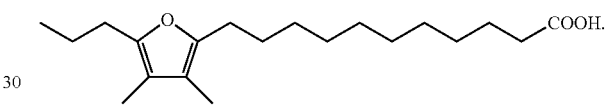

The compounds of the present invention can also be the salts and isomers thereof. In some embodiments, the compounds of the present invention include the salt forms thereof. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. These salts may be prepared by methods known to those skilled in art. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain basic acidic functionalities that allow the compounds to be converted into base addition salts. Additional information on suitable pharmaceutically acceptable salts can be found in Remington's Pharmaceutical Sciences, 17th ed., Mack Publishing Company, Easton, Pa., 1985, which is incorporated herein by reference.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another.

Unless otherwise stated, the compounds of the present invention may also contain unnatural proportions of atomic isotopes at one or more of the atoms that constitute such compounds. For example, the compounds of the present invention may be radiolabeled with radioactive isotopes, such as for example deuterium ($^2$H), tritium ($^3$H), iodine-125 ($^{125}$I), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the invention can be synthesized by a variety of methods known to one of skill in the art (see *Comprehensive Organic Transformations* Richard C. Larock, 1989) or by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. One of skill in the art will appreciate that other methods of making the compounds are useful in the present invention.

The compounds of the present invention can be prepared by a variety of methods known to one of skill in the art. The methods of making the compounds of the present invention can include any suitable protecting group or protecting group strategy. A protecting group refers to a compound that renders a functional group unreactive to a particular set of reaction conditions, but that is then removable in a later synthetic step so as to restore the functional group to its original state. Such protecting groups are well known to one of ordinary skill in the art and include compounds that are disclosed in "Protective Groups in Organic Synthesis", 4th edition, T. W. Greene and P. G M. Wuts, John Wiley & Sons, New York, 2006, which is incorporated herein by reference in its entirety.

V. Nutritional Supplements Including Furan Fatty Acid Compounds

In some embodiments, the present invention provides several nutritional supplements including FFA compounds. In some embodiments, the present invention provides nutritional supplements including a compound of Formula I having the structure:

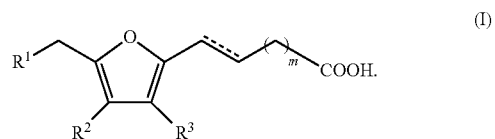

(I)

$R^1$ of Formula I can be $C_{1-18}$ alkyl. In some embodiments, $R^1$ is methyl, ethyl, or propyl. In some embodiments, $R^1$ is ethyl. $R^2$ and $R^3$ of Formula I can each independently be H or $C_{1-6}$ alkyl. In some embodiments, $R^2$ is H. In some embodiments, $R^2$ is methyl. In some embodiments, $R^3$ is H. In some embodiments, $R^3$ is methyl. In some embodiments, both $R^2$ and $R^3$ are H. In some embodiments, both $R^2$ and $R^3$ are methyl. Integer m of Formula I can be 1-18. In some embodiments, integer m is 6, 8, or 10. In some embodiments, integer m is 8.

In some embodiments, the compound of Formula I has the structure

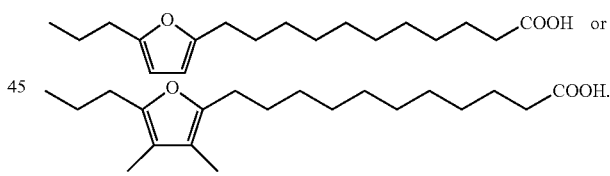

In some embodiments, the compound of Formula I has the structure

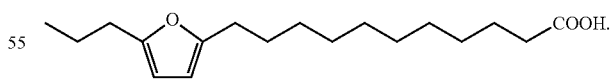

In some embodiments, the compound of Formula I has the structure

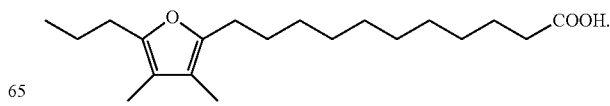

The nutritional supplement can be, for example, a nutraceutical, a dietary supplement, a food, or a food ingredient. The supplement can also serve as a natural food additive to, for example, prevent rancidity in fats The nutritional supplement can provide health benefits for a subject suffering from a heart disease, or having risk factors associated with an elevated occurrence or risk of heart disease. The heart disease can be, for example, atherosclerosis. The health benefits can include, for example, a change in the lipid composition in the blood of the subject.

The nutritional supplement can comprise any amount of the compounds disclosed herein, but will typically contain an amount determined to supply a subject with a desired dose of one or more furan fatty acids. The exact amount of compound required in the nutritional supplement will vary from subject to subject, depending on the species, age, weight, and general condition of the subject, the severity of the dietary deficiency being treated, and the particular mode of administration. The nutritional supplement can also comprise one or more other nutrients, such as a vitamin, mineral, trace essential element, amino acid, peptide, nucleic acid, oligonucleotide, lipid, cholesterol, steroid, thiosulfinate, or a carbohydrate. The nutritional supplement can also comprise other components such as preservatives, antimicrobials, antioxidants, chelating agents, thickeners, flavorings, diluants, emulsifiers, dispersing aids, or binders.

The nutritional supplement can further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; or potassium iodide. Suitable dosages for vitamins and minerals may be obtained, for example, by consulting the U.S. recommended daily allowance (RDA) guidelines.

The nutritional supplement can further comprise at least one food flavoring such as acetaldehyde (ethanal), acetoin (acetylmethylcarbinol), anethole (parapropenyl anisole), benzaldehyde (benzoic aldehyde), n-butyric acid (butanoic acid), d- or l-carvone (carvol), ciunamaldehyde (cinnamic aldehyde), citral (2,6-dimethyloctadien-2,6-al-8, geranial, neral), decanal (N-decylaldehyde, capraldehyde, capric aldehyde, caprinaldehyde, aldehyde C-10), ethyl acetate, ethyl butyrate, 3-methyl-3-phenyl glycidic acid ethyl ester (ethyl-methyl-phenyl-glycidate, strawberry aldehyde, C-10 aldehyde), ethyl vanillin, geraniol (3,7-dimethyl-2,6 and 3,6-octadien-1-ol), geranyl acetate (geraniol acetate), limonene (d-, l-, and dl-), linalool (linalol, 3,7-dimethyl-1,6-octadien-3-ol), linalyl acetate (bergamol), methyl anthranilate (methyl 1-2-amino benzoate), piperonal (3,4-methylenedioxy-benzaldehyde, heliotropin), vanillin, alfalfa (*Medicago sativa* L.), allspice (*Pimenta officinalis*), ambrette seed (*Hibiscus abelmoschus*), angelica (*Angelica archangelica*), Angostura (*Galipea officinalis*), anise (*Pimpinella anisum*), star anise (*Illicium verum*), balm (*Melissa officinalis*), basil (*Ocimum basilicum*), bay (*Laurus nobilis*), calendula (*Calendula officinalis*), (*Anthemis nobilis*), capsicum (*Capsicum frutescens*), caraway (*Carum carvi*), cardamom (*Elettaria cardamomum*), cassia (*Cinnamomum cassia*), cayenne pepper (*Capsicum frutescens*), Celery seed (*Apium graveolens*), chervil (*Anthriscus cerefolium*), chives (*Allium schoenoprasum*), coriander (*Coriandrum sativum*), cumin (*Cuminum cyminum*), elder flowers (*Sambucus canadensis*), fennel (*Foeniculum vulgare*), fenugreek (*Trigonella foenumgraecum*), ginger (*Zingiber officinale*), horehound (*Marrubium vulgare*), horseradish (*Armoracia lapathifolia*), hyssop (*Hyssopus officinalis*), lavender (*Lavandula officinalis*), mace (*Myristicafragrans*), majoram (*Majorana hortensis*), mustard (*Brassica nigra, Brassica juncea, Brassica hirta*), nutmeg (*Myristica fragrans*), paprika (*Capsicum annuum*), black pepper (*Piper nigrum*), peppermint (*Mentha piperita*), poppy seed (*Papayer somniferum*), rosemary (*Rosmarinus officinalis*), saffron (*Crocus sativus*), sage (*Salvia officinalis*), savory (*Satureia hortensis, Satureia montana*), sesame (*Sesamum indicum*), spearmint (*Mentha spicata*), tarragon (*Artemisia dracunculus*), thyme (*Thymus vulgaris, Thymus serpyllum*), turmeric (*Curcuma longa*), vanilla (*Vanilla planifolia*), zedoary (*Curcuma zedoaria*), sucrose, glucose, saccharin, sorbitol, mannitol, or aspartame. Other suitable flavoring are disclosed in such references as Remington's *Pharmaceutical Sciences*, 18th Edition, Mack Publishing, p. 1288-1300 (1990), and Furia and Pellanca, Fenaroli's *Handbook of Flavor Ingredients*, The Chemical Rubber Company, Cleveland, Ohio, (1971), known to those skilled in the art.

The nutritional supplement can further comprise at least one synthetic or natural food coloring, such as annatto extract, astaxanthin, beet powder, ultramarine blue, canthaxanthin, caramel, carotenal, beta carotene, carmine, toasted cottonseed flour, ferrous gluconate, ferrous lactate, grape color extract, grape skin extract, iron oxide, fruit juice, vegetable juice, dried algae meal, tagetes meal, carrot oil, com endosperm oil, paprika, paprika oleoresin, riboflavin, saffron, or turmeric.

The nutritional supplement can further comprise at least one phytonutrient, such as comprise at soy isoflavonoids, oligomeric proanthcyanidins, indol-3-carbinol, sulforaphone, fibrous ligands, plant phytosterols, ferulic acid, anthocyanocides, triterpenes, conjugated fatty acids such as conjugated linoleic acid and conjugated linolenic acid, polyacetylene, quinones, terpenes, cathechins, gallates, or quercitin. Sources of plant phytonutrients include, but are not limited to, soy lecithin, soy isoflavones, brown rice germ, royal jelly, bee propolis, acerola berry juice powder, Japanese green tea, grape seed extract, grape skin extract, carrot juice, bilberry, flaxseed meal, bee pollen, *ginkgo biloba*, red clover, burdock root, dandelion, parsley, rose hips, milk thistle, ginger, Siberian *ginseng*, rosemary, curcumin, garlic, lycopene, grapefruit seed extract, spinach, and broccoli.

The nutritional supplement can further comprise at least one vitamin, such as vitamin A, thiamin (B1), riboflavin (B2), pyridoxine (B6), cyanocobalamin (B12), biotin, ascorbic acid (vitamin C), retinoic acid (vitamin D), vitamin E, folic acid and other folates, vitamin K, niacin, or pantothenic acid. In some embodiments, the supplement comprises at least one mineral, such as sodium, potassium, magnesium, calcium, phosphorus, chlorine, iron, zinc, manganese, fluorine, copper, molybdenum, chromium, selenium, or iodine. In some embodiments, the nutritional supplement comprises a dosage of a plurality of vitamins or minerals in the range of the recommended daily allowance (RDA) as specified by the United States Department of Agriculture.

The nutritional supplement is typically prepared in an oral formulation. Oral preparations include tablets, pills, powder, dragees, capsules, liquids, lozenges, cachets, gels, syrups, slurries, suspensions, etc., suitable for ingestion. The nutritional supplement can be provided as a powder or liquid suitable for adding by a consumer to a food or beverage. In some embodiments, the nutritional supplement is administered to a subject in the form of a powder to be mixed into a beverage. In some embodiments, the nutritional supplement is stirred into a semi-solid food such as a pudding, topping, sauce, puree, cooked cereal, or salad dressing.

The nutritional supplement can also be in the form of a pharmaceutical compositions including a pharmaceutically acceptable carrier or excipient and a compound of the present invention. For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil, or coconut oil; in a fish oil or krill oil; in a mineral oil such as liquid paraffin; or in a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The nutritional supplement can be in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

VI. Examples

Example structures below are named according to standard IUPAC nomenclature using the CambridgeSoft ChemDraw naming package. Ethylmagnesium chloride (2M in THF), Ni(acac)$_2$, diallyl ether, lithium bis(trimethylsilyl) amide (LiHMDS, 1M in THF), 10-bromodecanoic acid (95%), palladium on carbon (5 wt % and 10 wt/o), hydrogen bromide (33 wt % in acetic acid) and triphenylphosphine were purchased from Sigma-Aldrich. Paraformaldehyde (96%) was purchased from Lancaster Synthesis. Triethylamine was purchased from EMD. All the reagents and solvents were used as received. 5-(Chloromethyl)furfural (Mascal and Nikitin (2008); and Mascal and Nikitin (2009)), 10-iododecanoic acid (Kling et al. (1993) *Chem. Soc. Perkin Trans.* 1183), and 2-(chloromethyl)-5-(dibutoxymethyl) furan (CMFDBA) (Chang et al. (2014) *J. Agric. Food Chem.* 62: 476) were prepared based on literature procedures.

Figure 2:
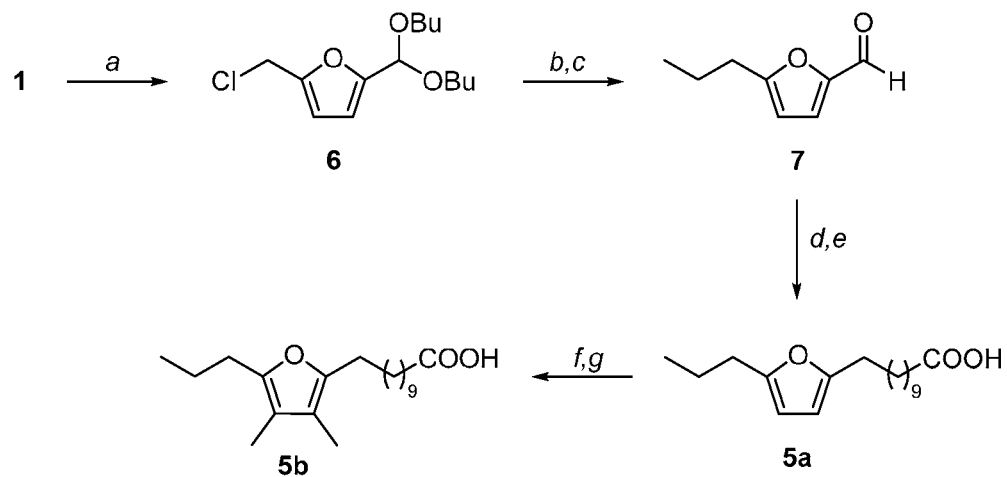
FIG. 2 is a scheme for the synthesis of furan fatty acids. Reagents and conditions include: (a) BuOH, HCl (cat.), 99%; (b) EtMgCl, Ni(acac)$_2$, diallyl ether (DAE), THF, −30° C.; (c) HCl/H$_2$O, 83% over 2 steps; (d) (9-carboxynonyl) triphenylphosphonium iodide, LiHMDS, THF/DMSO; (e) H$_2$ (balloon), Pd/C, THF, 92% over 2 steps; (f) paraformaldehyde, HBr, AcOH; (g) H$_2$ (1.2 bar), Pd/C, THF/H$_2$O, 80% over 2 steps.

Synthetic schemes are as shown in FIG. 2. An attractive starting point from 1 in the direction of 5 is the alkylation of the chloromethyl group via Kumada coupling. The involvement of an organometallic reagent in this reaction necessitated the protection of the aldehyde function in 1. We had previously described the simple reaction of 1 with butanol to give the dibutyl acetal 6 in essentially quantitative yield (Chang et al. (2014)). $Sp^3$-$sp^3$ coupling of 6 with ethylmagnesium chloride using the general method of Soler-Yanes, et al. ((2014) *Eur. J. Org. Chem.* 6625) followed by deprotection of the aldehyde function provided 5-propylfurfural 7 in 83% yield. Wittig reaction of 7 with the phosphonium ylide generated from 10-iododecanoic acid followed by hydrogenation of the olefinic bond gave the unmethylated FFA 5a ($n=1$, $m=9$, $R^1=R^2=H$) in 92% yield over both steps. Methylation of unsubstituted FFAs has been described by Lie Ken Jie and Wong but involves multiple steps, resulting in low yields (Lie Ken Jie and Wong (1991) *Lipids* 26: 836). We thus opted for a two-step bromomethylation-hydrodebromination protocol, which provided final product 5b ($n=1$, $m-=9$, $R^1=R^2=Me$) in 80%/yield. The selectivity in the hydrogenation of the di(bromomethyl) intermediate stems from the deactivating effect of the liberated halide on the Pd catalyst, which suppresses hydrogenation of the furan ring. The complete process from CMF 1 to 5b thus involves 7 steps and a 60% overall isolated yield.

Example 1. 5-Propylfuran-2-carbaldehyde

A flask was charged with CMFDBA 6 (1.013 g, 3.687 mmol), $Ni(acac)_2$ (56 mg, 0.22 mmol) and a stir bar. The vessel was evacuated and backfilled with argon, after which dry THF (20 mL) and diallyl ether (0.45 mL, 0.36 g, 3.7 mmol) were added. The mixture was stirred for 5 min and then cooled to −30° C. Ethyl magnesium chloride (2M in THF, 3.70 mL, 7.40 mmol) was added dropwise and the resulting yellow solution was stirred at −30° C. for 1 h. 1N HCl (100 mL) was added and the mixture was allowed to come to rt and stirred for 1 h. Dichloromethane (20 mL) was added, the mixture was agitated, and the organic layer was separated. The aqueous layer was extracted with dichloromethane (2×30 mL) and the combined organic layer was dried over $Na_2SO_4$. The solvent was evaporated and the residue was chromatographed on silica gel (15:1 hexanes/ethyl acetate) to give 7 as a yellow oil (0.421 g, 83%). $^1$H NMR (CDCl$_3$, 300 MHz): δ 9.51 (s, 1H), 7.16 (d, J=4.5 Hz, 1H), 6.23 (d, J=4.5 Hz, 1H), 2.69 (t, J=7.5 Hz, 2H), 1.72 (m, 2H), 0.97 (t, J=7.5 Hz, 3H). $^{13}$C NMR (CDCl$_3$, 75 MHz): δ 176.9, 163.9, 151.8, 123.5, 108.7, 30.3, 20.9, 13.6.

Example 2. 11-(5-Propylfuran-2-yl)undecanoic Acid

To a solution of (9-carboxynonyl)triphenylphosphonium iodide (0.788 g, 1.41 mmol) in 1:1 DMSO/THF (4 mL) was slowly added LiHMDS (1M in THF, 2.82 mL, 2.82 mmol) at 0° C. under argon and the mixture was stirred for 10 min. The resulting orange ylide solution was added dropwise to a stirred solution of 5-propylfuran-2-carbaldehyde 7 (0.194 g, 1.40 mmol) in THF (7 mL) and the mixture was stirred for 45 min at 0° C. The mixture was then poured into ice-cooled 1N HCl (100 mL). Ethyl acetate (30 mL) was added and the organic layer was separated. The aqueous layer was extracted with ethyl acetate (2×30 mL), the combined organic layer was dried over $Na_2SO_4$ and the solvent was evaporated. The olefin intermediate was obtained as an orange oil after flash chromatography through a short silica gel column (4:1 hexanes/EtOAc). To a solution of this product in THF (10 mL) was added 5 wt % Pd/C (45 mg). The reaction flask was gently evacuated, backfilled with hydrogen, and mounted with a hydrogen-filled balloon. The reaction mixture was stirred at rt for 6 h and then filtered through a thin layer of Celite. The Celite was washed with EtOAc and the filtrate was evaporated to give 5a as a white solid (0.380 g, 92%). $^1$H NMR (CDCl$_3$, 300 MHz): δ 5.84 (s, 2H), 2.58-2.52 (m, 4H), 2.35 (t, J=7.5 Hz, 2H), 1.70-1.53 (m, 6H), 1.42-1.19 (br, 12H), 0.95 (t, J=7.5 Hz, 3H). $^{13}$C NMR (CDCl$_3$, 75 MHz): δ 180.3, 154.6, 154.4, 104.9, 104.8, 34.1, 30.1, 29.5, 29.4, 29.3, 29.2, 29.2, 29.0, 28.1, 28.1, 24.7, 21.5, 13.8. HRMS: $C_{18}H_{29}O_3$ ([M-H]$^-$), calculated: 293.2122, found: 293.2117.

Example 3. 11-(3,4-Dimethyl-5-propylfuran-2-yl)undecanoic Acid

To a solution of 1-(5-propylfuran-2-yl)undecanoic acid 5a (0.152 g, 0.516 mmol) and paraformaldehyde (50 mg, 1.7 mmol) in acetic acid (10 mL) at 15° C. was slowly added hydrobromic acid (33 wt % in acetic acid, 0.28 mL, 0.39 g, 1.6 mmol). The reaction mixture was allowed to warm to rt and stirred for 3 h. Saturated aq. NH$_4$Cl (20 mL) was added and the mixture was extracted with EtOAc (3×30 mL). The organic layers were combined, dried over $Na_2SO_4$, and concentrated to a volume of about 3 mL. 1:1 THF/H$_2$O (40 mL) and 10 wt % Pd/C (25 mg) were added and the reaction vessel was purged with hydrogen (×3) and pressurized to 17 psi (1.2 bar) H$_2$. The mixture was shaken in a Parr hydrogenator for 3 h, during which the initial pressure was maintained. The hydrogen was released and the mixture was extracted with EtOAc (3×30 mL). The organic layers were combined and the solvent was evaporated. The crude product was chromatographed on silica gel through a short flash column (5:1 hexanes/EtOAc) to give 5b as a colorless oil (0.134 g, 80%). $^1$H NMR (CDCl$_3$, 300 MHz): δ 2.50-2.44 (m, 4H), 2.35 (t, J=7.5 Hz, 2H), 1.83 (s, 6H), 1.68-1.48 (m, 6H), 1.37-1.20 (br, 12H), 0.90 (t, J=7.5 Hz, 3H). $^{13}$C NMR (CDCl$_3$, 75 MHz): δ 180.4, 148.4, 148.2, 114.6, 114.4, 34.1, 29.7, 29.5, 29.4 (29.41), 29.4 (29.38), 29.3, 29.2, 29.1, 28.8, 28.1, 26.1, 24.7, 22.1, 13.8, 8.4. HRMS: $C_{20}H_{33}O_3$ ([M-H]$^-$), calculated: 321.2435, found: 321.2434.

Example 4. 22-Diphenyl-1-picrylhydrazyl (DPPH) Assay

The antioxidant activity of the FFAs has been evaluated by a range of methods, including spin trapping of N-oxide radicals (Okada et al. (1996) *Biol. Pharm. Bull.* 19: 1607), inhibition of radically initiated oxygen uptake in linoleic acid (Okada et al. (1990) *J. Am. Oil Chem. Soc.* 67: 858) and unsaturated fatty acid moieties of phosphatidyl choline liposomes (Ishii et al. (1989) *Chem. Pharm. Bull.* 37: 1396), and acting as a substrate for plant lipoxygenase (Batna and Spiteller (1994) *Lipids* 29: 397). We have evaluated the free radical scavenging abilities of synthetic FFAs 5a ($n=1$, $m=9$, $R^1=R^2=H$) and 5b ($n=1$, $m=9$, $R^1=R^2=Me$) against butylated hydroxytoluene (BHT) by 2,2-diphenyl-1-picrylhydrazyl (DPPH) assay.

The method of Moon and Shibamoto (Moon and Shibamoto (2009) *J. Agric. Food Chem.* 57: 1655) was used to evaluate antioxidant activity. DPPH (0.0177 g) was dissolved in methanol (MeOH) (100 mL) and 500 µL of this solution was added into test tubes containing 11-(5-propylfuran-2-yl)undecanoic acid and 11-(3,4-dimethyl-5-propylfuran-2-yl)undecanoic acid at concentrations of 25, 50, and 100 µg/mL after dilution of stock solutions with MeOH to 1.0 mL total volume. A 1.0 mg/mL BHT stock solution (100 µL) was diluted with 400 µL methanol and the DPPH solution (500 µL). A control solution was prepared by adding methanol (500 µL) into the DPPH solution (500 µL), and a methanol blank was used for the baseline correction. The tubes were allowed to stand at room temperature in the dark for 30 minutes and the change in the absorption at 517 nm was measured by UV-visible spectrometry. Radical scavenging ability was expressed as DPPH scavenging % and calculated using this formula: DPPH scavenging %=(control abs.−sample abs./control abs.)×100.

Figure 3:
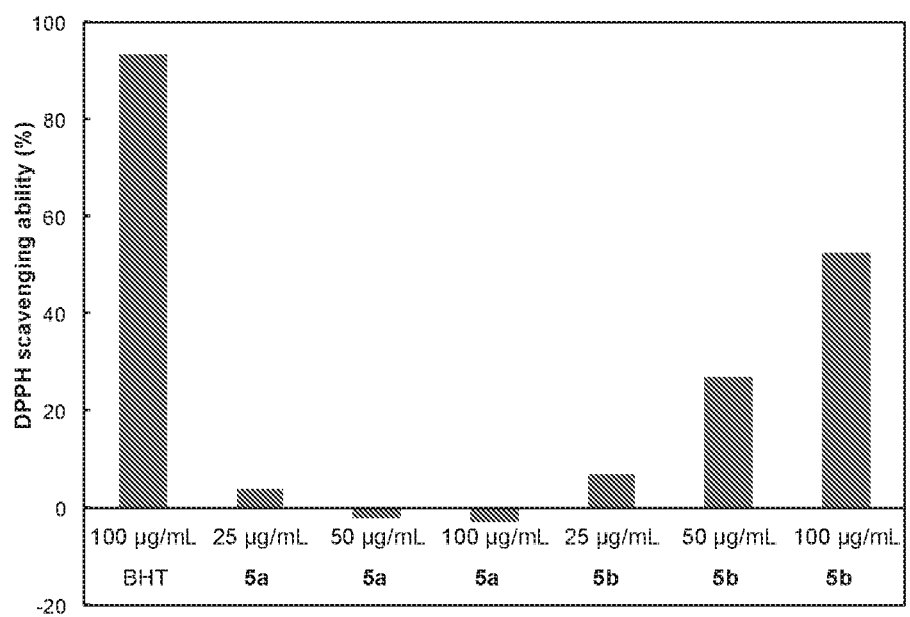
FIG. 3 is a graph of results from a 2,2-diphenyl-1-picrylhydrazyl assay of the antioxidant activities of 11-(5-propylfuran-2-yl)undecanoic acid and 11-(3,4-dimethyl-5-propylfuran-2-yl)undecanoic acid.

The results of the antioxidant activity assay are given in Table 1 below and rendered graphically in FIG. 3. As can be seen, the unmethylated FFA has virtually no antioxidant activity, while the dimethylated FFA shows concentration-dependent quenching of the DPPH radical. At 100 pig/mL, dimethylated FFA exhibits 53% inhibition against BHTs 93% inhibition. Thus, the FFA has 57% of the antioxidant power of BHT on a mass basis. Recalculating based on molar concentrations increases that value to 83%. Thus, while BHT performs marginally better in the DPPH assay, the incorporation of 5 into human phospholipids argues a much greater role in the protection against inflammation than does raw antioxidant power (Spiteller (2005) *Mol. Nutr. Food Res.* 49: 999). Indeed, given concerns about the toxicity of synthetic radical scavengers like BHT, FFAs could also serve as natural food additives, in particular in preventing rancidity in fats.

TABLE 1

Radical scavenging abilities of furan fatty acids by DPPH assay

| Compound | DPPH Scavenging % |
|---|---|
| 5a (25 µg/mL) | 4 |
| 5a (50 µg/mL) | −2 |
| 5a (100 µg/mL) | −3 |
| 5b (25 µg/mL) | 7 |
| 5b (50 µg/mL) | 27 |
| 5b (100 µg/mL) | 53 |
| BHT (100 µg/mL) | 93 |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for preparing a compound of Formula I having the structure:

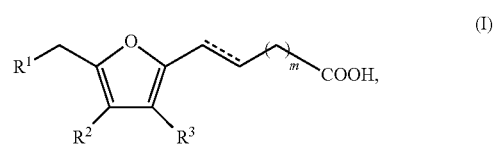

the method comprising:
forming a reaction mixture comprising an aqueous acid and a compound of Formula IV:

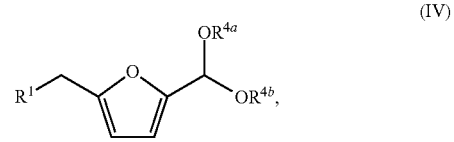

under conditions sufficient to form a compound of Formula V:

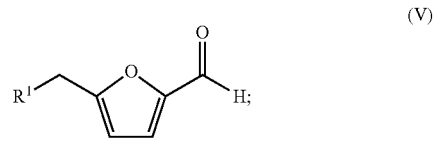

forming a reaction mixture comprising a phosphonium salt of Formula VI:

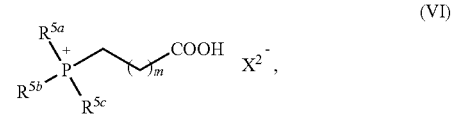

and the compound of Formula V, under conditions sufficient to form a compound of Formula (Ia) having the structure:

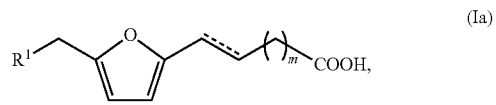

wherein $R^{5a}$, $R^{5b}$, and $R^{5c}$ are each independently selected from the group consisting of H, $C_{1-18}$ alkyl, $C_{2-18}$ alkenyl, and $C_{6-12}$ aryl, and $X^2$ is halogen;
forming a reaction mixture comprising formaldehyde or paraformaldehyde, hydrogen bromide, and the compound of Formula (Ia), under conditions sufficient to form a compound of Formula VII:

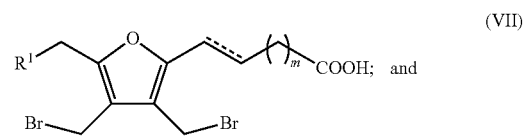

forming a reaction mixture comprising hydrogen, a hydrogenation catalyst, and the compound of Formula VII under conditions sufficient to form the compound of Formula I, wherein
$R^1$ is $C_{1-18}$ alkyl;
$R^2$ and $R^3$ are methyl groups;
$R^{4a}$ and $R^{4b}$ are each independently $C_{1-18}$ alkyl; and
m is an integer from 1 to 18.

2. The method of claim 1, wherein the aqueous acid is hydrochloric acid.

3. The method of claim 1, wherein m is 8, $X^2$ is iodine, and $R^{5a}$, $R^{5b}$, and $R^{5c}$ are each phenyl.

4. The method of claim 1, further comprising
forming a reaction mixture comprising hydrogen, a second hydrogenation catalyst, and the compound of Formula Ia having the structure:

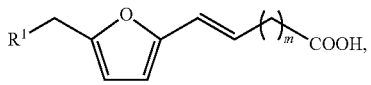

under conditions sufficient to form the compound of Formula Ia having the structure:

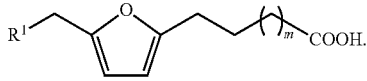

5. The method of claim 1, wherein the compound of Formula I has the structure:

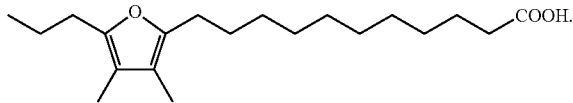 [SMILES: CCCc1oc(CCCCCCCCCCC(=O)O)c(C)c1C]

6. The method of claim 1, further comprising:
forming a reaction mixture comprising an alkylating agent with a Formula $R^1ML_n$, and a compound of Formula III:

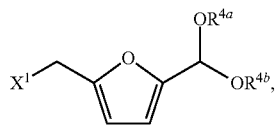

under conditions sufficient to form the compound of Formula IV, wherein $X^1$ is halogen, M is a metal, L is a ligand, and n is an integer from 1 to 3.

7. The method of claim 6, wherein the alkylating agent has the Formula $R^1MgX^3$, wherein $X^3$ is halogen.

8. The method of claim 6, wherein the alkylating agent is ethylmagnesium chloride.

9. The method of claim 6, wherein $X^1$ is chlorine.

10. The method of claim 6, further comprising:
forming a reaction mixture comprising an alcohol and a compound of Formula II:

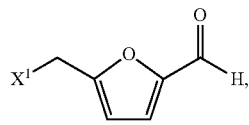

under conditions sufficient to form the compound of Formula III.

11. The method of claim 10, wherein the alcohol is butanol.

12. The method of claim 10, wherein the compound of Formula I has the structure:

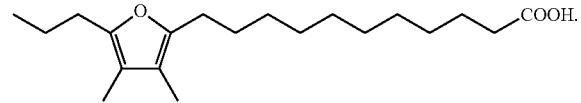 [SMILES: CCCc1oc(CCCCCCCCCCC(=O)O)c(C)c1C]

* * * * *